United States Patent
Omaleki et al.

(10) Patent No.: US 6,228,072 B1
(45) Date of Patent: *May 8, 2001

(54) SHAFT FOR MEDICAL CATHETERS

(75) Inventors: Samuel L. Omaleki, Morgan Hill; Roy Leguidleguid, Union City; Ketan P. Muni, San Jose, all of CA (US)

(73) Assignee: PercuSurge, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,105

(22) Filed: Feb. 19, 1998

(51) Int. Cl.$^7$ .................................................. A61M 25/00
(52) U.S. Cl. .......................................... 604/529; 604/500
(58) Field of Search ................................... 604/529, 523, 604/524, 264, 500

(56) References Cited

U.S. PATENT DOCUMENTS

| | | |
|---|---|---|
| 3,539,674 | 11/1970 | Dereniuk et al. . |
| 4,345,602 | 8/1982 | Yoshimura et al. . |
| 4,545,390 | 10/1985 | Leary . |
| 4,582,181 | 4/1986 | Samson . |
| 4,616,653 | 10/1986 | Samson et al. . |
| 4,637,396 | 1/1987 | Cook . |
| 4,655,746 | 4/1987 | Daniels et al. . |
| 4,661,094 | 4/1987 | Simpson . |
| 4,723,936 | 2/1988 | Buchbinder et al. . |
| 4,737,219 | 4/1988 | Taller et al. . |
| 4,748,982 | 6/1988 | Horzewski et al. . |
| 4,763,654 | 8/1988 | Jang . |
| 4,771,777 | 9/1988 | Horzewski et al. . |
| 4,784,636 | 11/1988 | Rydell . |
| 4,790,315 | 12/1988 | Mueller, Jr. et al. . |
| 4,921,483 | 5/1990 | Wijay et al. . |
| 5,102,390 | 4/1992 | Crittenden et al. . |
| 5,169,386 | 12/1992 | Becker et al. . |
| 5,203,777 | * 4/1993 | Lee ....................... 604/529 |
| 5,320,604 | 6/1994 | Walker et al. . |
| 5,360,397 | 11/1994 | Pinuchuk . |
| 5,387,225 | 2/1995 | Euteneuer et al. . |
| 5,489,277 | * 2/1996 | Tolkoff et al. ............ 604/529 |
| 5,558,652 | * 9/1996 | Henke ..................... 604/529 |
| 5,593,419 | 1/1997 | Segar . |
| 5,593,718 | 1/1997 | Conway et al. . |
| 5,605,543 | 2/1997 | Swanson . |
| 5,630,806 | * 5/1997 | Inagaki et al. ............ 604/529 |
| 5,766,202 | * 6/1998 | Jones et al. .............. 604/529 |

FOREIGN PATENT DOCUMENTS

| | | |
|---|---|---|
| 0 761 253 A2 | 9/1995 | (EP) . |
| 0 778 042 A2/A3 | 12/1995 | (EP) . |
| 0 778 037 A1 | 6/1997 | (EP) . |
| WO 91/13649 | 9/1991 | (WO) . |
| WO 92/00775 | 1/1992 | (WO) . |
| WO 96/38193 | 12/1996 | (WO) . |
| WO 97/44084 | 11/1997 | (WO) . |

* cited by examiner

Primary Examiner—John D. Yasko
(74) Attorney, Agent, or Firm—Knobbe, Martens, Olson & Bear LLP

(57) ABSTRACT

Several improvements are provided in the design of a catheter shaft to reduce costs and improve performance. In one aspect, a small notch is fabricated into a catheter tube by a nonlaser process such as electric discharge machining (EDM) or mechanical grinding. This notch in the catheter tube is necessary for fluid communication between the catheter lumen and a balloon or other element in communication with the tube. Use of a nonlaser process reduces the costs of fabrication while ensuring a high degree of structure integrity. In another aspect, a method is provided to produce a nonuniform polymer coating on a catheter shaft to reduce friction and to maintain a catheter with a low profile. In another aspect, the catheter is provided with a radiopaque marker which is more visible and is more effective at identifying the location of a balloon. The marker is moved closer to a distal balloon by placing it within an adhesive taper adjacent the balloon.

8 Claims, 3 Drawing Sheets

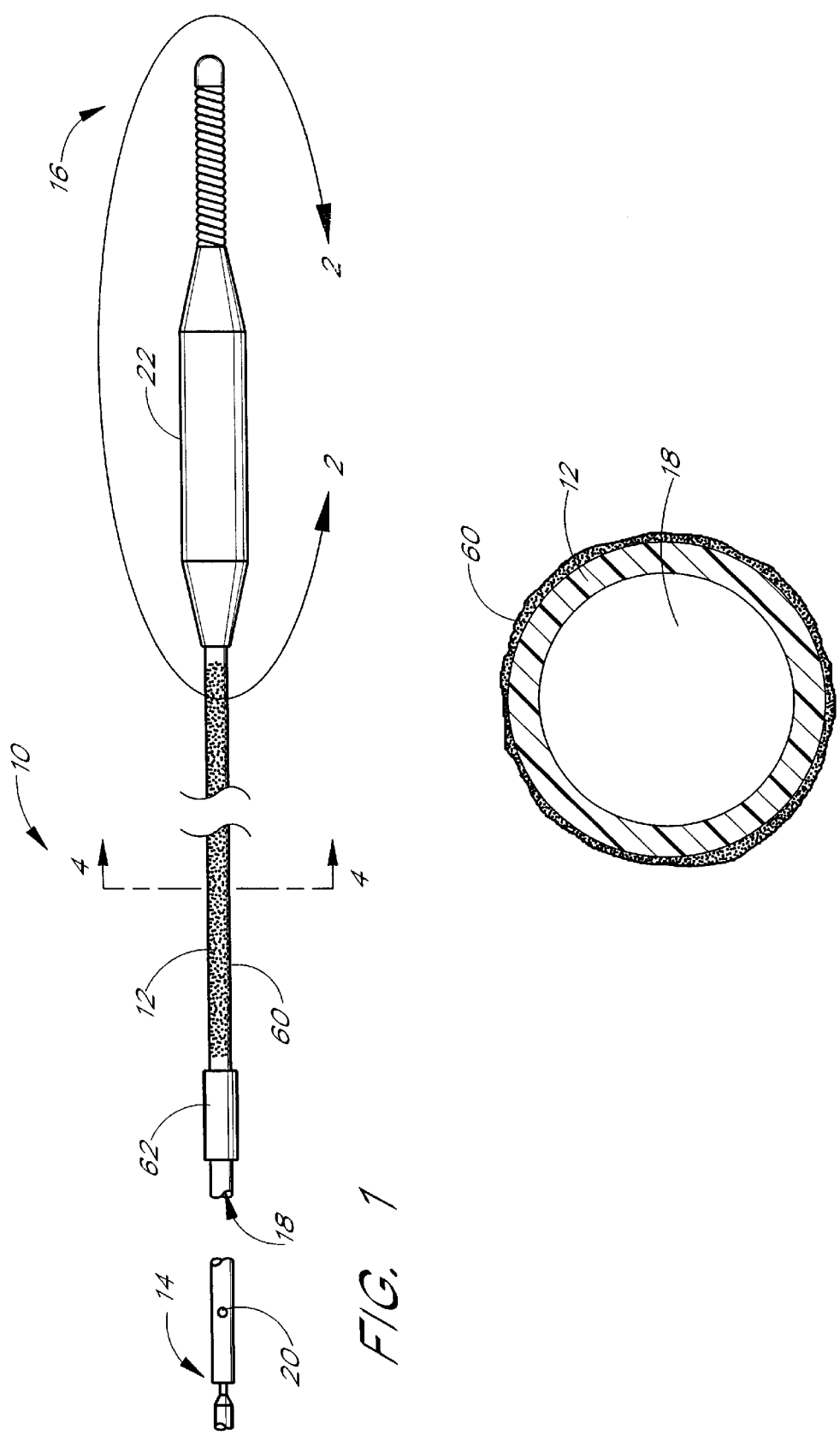

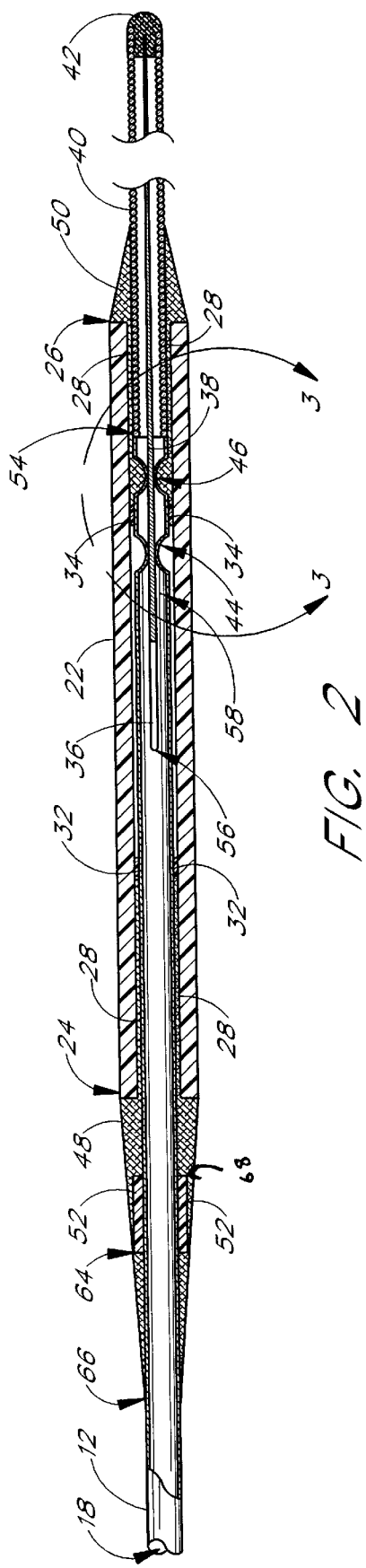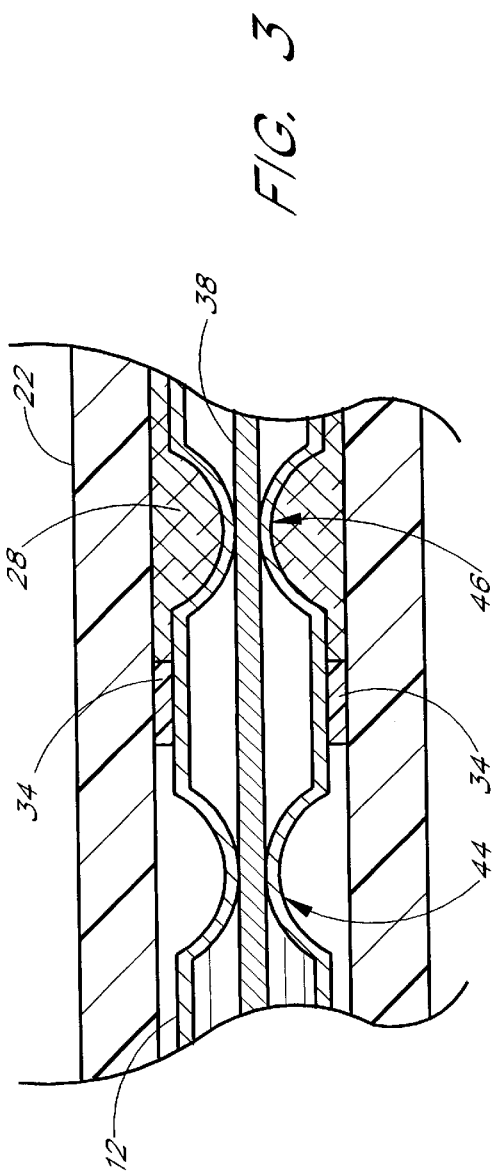

SHAFT FOR MEDICAL CATHETERS

BACKGROUND OF THE INVENTION

1. Field of the Invention

The present invention relates generally to surgical device design and fabrication and, more particularly, to a shaft for medical catheters.

2. Background of the Invention

Medical catheters, such as balloon catheters, have been proven efficacious in treating a wide variety of blood vessel disorders. Moreover, these types of catheters have permitted clinicians to treat disorders with minimally invasive procedures that, in the past, would have required complex and perhaps life threatening surgeries. For example, balloon angioplasty is now a common procedure to alleviate stenotic lesions (i.e., clogged arteries) in blood vessels, thereby reducing the need for heart bypass operations.

Previously known catheters are of complex construction, requiring expensive manufacturing steps and construction of great precision to navigate the tortuous pathways of a vessel network. For instance, when a catheter provides inflation fluid to a balloon, a small notch is typically provided in the catheter tube to allow fluid to pass from a lumen within the tube to the balloon. The conventional method for manufacturing this notch is with a laser, which is expensive and often cannot be done in-house. Further, use of a laser creates a heat-affected zone which can lead to fracture of the notch. Moreover, the heat from the laser may cause deformation of the material. This is especially problematic when a straight catheter made of a nickel-titanium alloy is desired. Because the properties of NiTi alloys are extremely temperature sensitive, laser notching may cause buckling or unwanted curvature in the material. Accordingly, there is a need for a notch-forming process which will not cause damage to the material.

Further, profile is often a concern for catheters because of the small space in which the catheters will be inserted. In addition, because catheters must be passed through a tortuous blood vessel network to reach the intended treatment site, it is desirable that the catheters be substantially frictionless to reduce harmful contact with blood vessel walls. Catheters therefore are generally provided with a coating that will increase lubricity of the catheter. These coatings add additional, undesired size to the catheter. Thus, there is a need for a substantially frictionless catheter surface which does not add significant profile to a catheter tube.

In navigating the pathways of a vessel network, a radiopaque marker is often necessary to identify a specified location on the catheter. Such markers are typically placed on the catheter tube near the location of a distal balloon. However, in medical devices employing aspiration catheters and the like, visibility problems often arise with such markers because they are typically made small in order to allow the aspiration catheter to be passed over the marker as it extends towards the distal balloon. Accordingly, there is a need for balloon catheters having markers which can better identify the location of a balloon while inside a blood vessel.

SUMMARY OF THE INVENTION

The present invention addresses the needs raised above by providing several improvements in the design of a shaft for medical catheters. In one aspect, a small notch is fabricated into a catheter tube by a nonlaser process such as electric discharge machining (EDM) or mechanical grinding. This notch in the catheter tube is necessary for fluid communication between the catheter lumen and a balloon or other element in communication with the tube. Use of a nonlaser process reduces the costs of fabrication while ensuring a high degree of structural integrity.

In another aspect of the present invention, a method is provided to produce a thinner coating on a catheter shaft to reduce friction with vessel walls. To maintain a surface with a low friction coefficient while keeping the profile of the catheter low, the catheter is sputter coated with Teflon or similar material to produce a nonuniform coating. This nonuniform coating may extend 360 degrees around the catheter tube, and may even provide a coating of less than 360 degrees while still maintaining good lubricity.

In yet another aspect, a catheter wire or tube is provided with a radiopaque marker which is more visible and is more effective at identifying the location of a balloon on the catheter. The marker is moved closer to a distal balloon by placing it within an adhesive taper adjacent the balloon. By placing the marker in the taper, the marker can be made larger and more visible without obstructing the placement of an aspiration catheter or other type of catheter over the catheter wire or tube. Specifically, the marker in being placed inside the taper and closer to the balloon can act as a stopper to the aspiration catheter and prevent damage to the balloon.

BRIEF DESCRIPTION OF THE DRAWINGS

FIG. 1 is a side view of the catheter of the present invention.

FIG. 2 is a longitudinal cross-sectional view of the distal end of a catheter having the improvements of the present invention.

FIG. 3 is an enlarged cross-sectional view along area 3—3 of FIG. 2.

FIG. 4A is a cross-sectional view along line 4—4 of FIG. 1 showing a nonuniform coating on the catheter.

DETAILED DESCRIPTION OF THE PREFERRED EMBODIMENTS

Figure 4B:
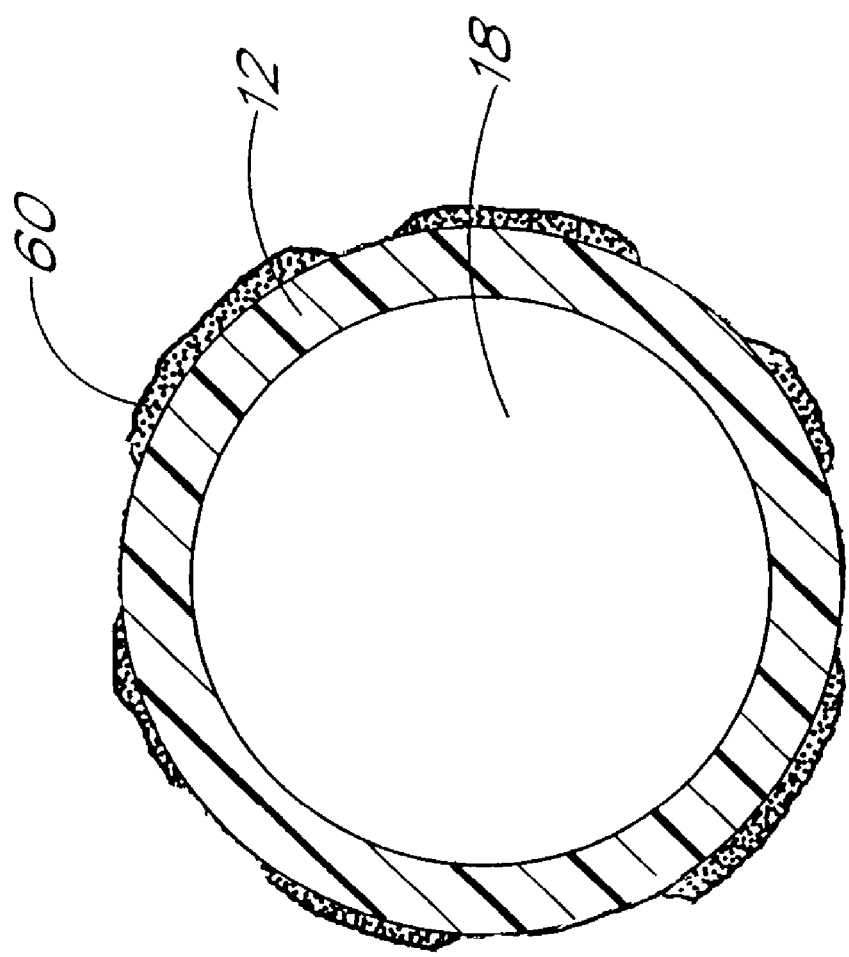
FIG. 4B is a cross-sectional view along line 4—4 of FIG. 1 showing an alternate embodiment of a nonuniform coating on the catheter.

Referring to FIG. 1, there is depicted a catheter 10 incorporating the improvements of the present invention. Although the improvements of the present invention are depicted and discussed in the context of being part of a simple occlusive device having a single lumen, it should be appreciated that the present invention is applicable to more complex occlusive devices having structures and functionalities not discussed herein. For example, the present inventors contemplate that the improvements of the present invention may be used in occlusive devices functioning as anchorable guide wires or filters. In addition, the improvements of the present invention are also applicable to catheters having other types of balloons, such as latex or silicone, or to catheters having dilatation balloons, made of materials such as polyethylene terephthalate. Moreover, the improvements of the present invention may also be adapted to other types of catheters used in drug delivery or radiation therapy, such as irrigation catheters, and to catheters having no balloon at all. The manner of adapting the improvements of the present invention to these various structures and functionalities will become readily apparent to those of skill in the art in view of the description which follows.

In FIG. 1, an occlusion balloon catheter 10 is shown. Catheter 10 generally comprises an elongate flexible shaft or tubular body 12 extending between a proximal control end 14, corresponding to a proximal section of tubular body 12, and a distal functional end 16, corresponding to a distal section of tubular body 12. Tubular body 12 has a central lumen 18 which extends between ends 14 and 16. An inflation port 20 is provided on tubular body 12 near the proximal end 14. Inflation port 20 is in fluid communication with lumen 18, such that fluid passing through inflation port 20 into or out of lumen 18 may be used to inflate or deflate inflation balloons in communication with lumen 18. Lumen 18 is sealed fluid tight at distal end 16. Inflation port 20 may be similar to existing female luer lock adapters or would be a removable valve at the end, as disclosed in assignee's co-pending application entitled LOW PROFILE CATHETER VALVE AND INFLATION ADAPTER, application Ser. No. 08/975,723 filed Nov. 20, 1997, the entirety of which is incorporated by reference.

The length of tubular body 12 may be varied considerably depending upon the desired application. For example, where catheter 10 serves as a guidewire for other catheters in a conventional percutaneous transluminal coronary angioplasty procedure involving femoral artery access, tubular body 12 is comprised of a hollow hypotube having a length in the range of from about 160 to about 320 centimeters with a length of about 180 centimeters being optimal for a single operator device and 300 centimeters for over the wire applications. Alternately, for a different treatment procedure, not requiring as long a length of tubular body 12, shorter lengths of tubular body 12 may be provided. Moreover, the catheter 10 may comprise a solid shaft rather than a hollow hypotube.

Tubular body 12 generally has a circular cross-sectional configuration with an outer diameter within the range of from about 0.008 inches to 0.14 inches. In many applications where catheter 10 is to be used as a guidewire for other catheters, the outer diameter of tubular body 12 ranges from 0.010 inches to 0.038 inches, and preferably is about 0.014 to 0.018 inches in outer diameter or smaller. Noncircular cross-sectional configurations of lumen 18 can also be adapted for use with the present invention. For example, triangular, rectangular, oval, and other noncircular cross-sectional configurations are also easily incorporated for use with the present invention, as will be appreciated by those of skill in the art.

Tubular body 12 has sufficient structural integrity, or "pushability," to permit catheter 10 to be advanced through vasculature to distal arterial locations without buckling or undesirable kinking of tubular body 12. It is also desirable for tubular body 12 to have the ability to transmit torque, such as in those embodiments where it may be desirable to rotate tubular body 12 after insertion into a patient. A variety of biocompatible materials, known by those of skill in the art to possess these properties and to be suitable for catheter manufacture, may be used to produce tubular body 12. For example, tubular body 12 may be made of stainless steel such as Elgiloy (TM), or may be made of polymeric materials such as nylon, polyimide, polyamides, polyethylene or combinations thereof. In one preferred embodiment, the desired properties of structural integrity and torque transmission are achieved by forming tubular body 12 out of an alloy of titanium and nickel, commonly referred to as nitinol. In a preferred embodiment, the nitinol alloy used to form tubular body 12 is comprised of about 50.8% nickel and the balance titanium, which is sold under the trade name Tinel (TM) by Memry Corporation. It has been found that a catheter tubular body having this composition of nickel and titanium exhibits an improved combination of flexibility and kink resistance in comparison to other materials. Further details are disclosed in assignee's co-pending applications entitled HOLLOW MEDICAL WIRES AND METHODS OF CONSTRUCTING SAME, application Ser. No. 08/812,876, filed on Mar. 6, 1997, CATHETER BALLOON CORE WIRE, application Ser. No. 08/813,024, filed Mar. 6, 1997, and CORE WIRE WITH SHAPEABLE TIP, application Ser. No. 09/026,357, filed Feb. 19, 1998, all of which are hereby incorporated by reference in their entirety.

As illustrated in FIG. 1, an expandable member such as an inflatable balloon 22 is mounted on tubular body 12. Balloon 22 may be secured to tubular body 12 by any means known to those skilled in the art, such as adhesives or heat bonding. In one preferred embodiment, balloon 22 is a compliant balloon formed out of a material comprising a block polymer of styrene-ethylene-butylene-styrene (SEBS). As shown in FIGS. 2 and 3, balloon 22 has a proximal end 24 and a distal end 26 which are both secured to the outer surface of tubular body 12. Balloon 22 may be secured to the tubular body 12 by any means known to those of skill in the art, such as adhesives or heat bonding. FIGS. 2 and 3 show the use of adhesives 28 bonding the balloon at its proximal end 24 and distal end 26, respectively, up to adhesive stops 32 and 34, the distance between the adhesive stops defining the working length of the balloon. Further details are disclosed in assignee's co-pending application entitled BALLOON CATHETER AND METHOD OF MANUFACTURE, application Ser. No. 09/026,225, filed Feb. 19, 1998, the entirety of which is hereby incorporated by reference.

A notch 36 is provided in the tubular body 12, as shown on the back side of tubular body 12 in FIG. 2, within the working length of the balloon to provide fluid communication between the lumen 18 and the balloon 22. A core wire 38 is provided at the distal end of the tubular body 12, inserted into the lumen 18 so that part of the core wire 38 is visible through the notch 36. Coil 40 surrounds the core wire 38 and is soldered at a distal end into a rounded tip 42. The core wire 38 is secured within the lumen 18 of tubular body 12 by a combination of adhesive bonding and crimping at points 44 and 46 of the tubular body 12. Tapers 48 and 50 are shown at the proximal and distal ends of the balloon 22, respectively. A radiopaque marker 52 is located within the proximal taper 48.

The core wire 38 and the coil 40 are formed into a subassembly prior to attachment to tubular body 12. Once the coil 40 is attached to the core wire, a proximal end of core wire 38 is inserted into tubular body 12 at distal end 54. Two crimps 44 and 46 are provided near the distal end 54 of the tubular body 12 to secure the core wire 38 to the tubular body. The crimps are preferably located in a location between the notch 36 and the distal end 54 of the tubular body 12. The crimps are preferably located a distance 0.5 to 1.5 mm apart, and more preferably, about 1.0 mm apart. The more distal crimp 46 preferably is located about 0.5 mm from the distal end 54 of tubular body 12. Further details are disclosed in the above-referenced application CORE WIRE WITH SHAPEABLE TIP, application Ser. No. 09/026,357, filed Feb. 19, 1998.

Fabrication of the Notch

In one aspect of the present invention, the notch 36 shown in FIG. 2 is formed by a nonlaser process. Preferably, the process used is electric discharge machining (EDM). This method allows removal of metal by a series of rapidly recurring electrical discharges between an electrode (the cutting tool) and the workpiece in the presence of a liquid (usually hydrocarbon dielectric). Using EDM, the notch 36 can be made economically but also with great precision. The notch 36 preferably has a length between 0.001 and 0.005 inches and a width between 0.001 and 0.005 inches, depending on the working length of the balloon 22 and the diameter of the tubular body 12. As shown in FIG. 2, when the distance between the inner surfaces of the adhesive stops 32 and 34 is 4 mm and the outer diameter of the tubular body 12 is 0.0132 inches, the notch 36 preferably has a length of 1.5 mm and a width of 0.003 inches. The notch 36 may be centered within the working length of the balloon, such that the distance between the ends of the notch and each of the adhesive stops 32 and 34 is the same. Alternatively, when the core wire 38 extends into the lumen 18 of the tubular body 12 and is visible in the notch 36, the location of the notch 36 may be shifted towards distal end 54 of the tubular body. In FIG. 2, where the distance between adhesive stops 32 and 34 is 4 mm, the core wire 38 extends 0.5 mm into the notch 36. The notch 36 is 1.5 mm long, with the proximal end 56 of the notch 36 located a distance 1.5 mm from the first adhesive stop 32, and the distal end 58 of the notch 36 located 1 mm from the second adhesive stop 34.

To manufacture the notch, preferably, an EDM with a 0.0055±0.0005 inch electrode is used. A current of 0.5 amps is applied, with an on time of 6 seconds and an off time of 50 seconds. Although the EDM processing of the notch has been described with respect to specific parameters, it should be recognized that other parameters as well may be used for the EDM. Furthermore, EDM may be used not only for fabrication of a distal notch to inflate a balloon, but also for a notch such as inflation port 20 at the proximal end of the tubular body as shown in FIG. 1, or other types of notches that may be provided for a medical catheter.

Although fabrication of the notch has been described with reference to an EDM procedure, other nonlaser processes may be used as well. For instance, mechanical grinding is another low cost procedure for fabricating a notch that can be performed in-house.

Nonuniform Coating

In another aspect of the present invention, the shaft or tubular body 12 is sputter-coated with a polymeric material to reduce friction between the catheter and blood vessels and produce a lubricious, nonuniform coating on the tubular body 12. As used herein, "nonuniform" refers either to a coating that is variable in thickness along the circumference or length of the body 12, or to a coating which covers the body 12 in some areas but not at all in others. As shown in FIG. 1, a coating 60 is applied to the tubular body 12 between a proximal marker 62 and the balloon 22. The coating begins at a distance preferably within about 5 mm of the marker 62, and more preferably within about 2 mm. The coating 60 terminates preferably within about 1 cm of the proximal taper 48. Preferred coating materials include polytetrafluoroethylene (TFE), with Teflon being a desired material for the coating 60. Those skilled in the art will recognize that similar materials with high lubricity may be used.

As shown in FIGS. 4A and 4B, a nonuniform coating 60 adds very little dimension to the tubular body 12. FIG. 4A shows one embodiment where the coating 60 is thin with a variable thickness that covers substantially the entire circumference of the tubular body 12. FIG. 4B shows another embodiment where the coating 60 is thin but does not coat the entire circumference of tubular body 12. Thicknesses in the range of about 0.001 to about 0.0035 inches are preferred. In both of the embodiments shown in FIGS. 4A and 4B, preferably, the coating 60 has a thickness of no greater than about 0.01 inches, and more preferably, the coating thickness is no greater than about 0.0035 inches. Thus, it has been discovered that sufficient lubricity can be achieved with a nonuniform or even intermittent, sporadic coating, while simultaneously maintaining a low profile.

To apply the polymeric coating 60 to the tubular body 12, the surface of the tubular body 12 is first cleaned. Preferable cleaning methods are by preparing a cleaning solvent blend using a 1:1 (by volume) mixture of acetone and isopropyl alcohol. The tubular body 12 may be cleaned by wiping the body with a lint-free towel or cloth wetted by this solvent blend. After the solvent wipe, the tubular body 12 is heat cleaned in an oven for 15 minutes at 540° F.

The Teflon coating solution may be Xylan 1006/870 Black Teflon coating as obtained from Whitford Corporation. To achieve a thinner film thickness, the coating can be mixed with a thinner such as thinner #99B from Whitford Corporation. To mix the coating solution with the thinner, the coating solution is first mixed well in a container using a mechanical stirrer for about 5 to 10 minutes to remove residue and Teflon particles from the bottom of the container. About 80 parts by volume of the coating solution is mixed with about 20 parts by volume of the thinner with a mechanical stirrer until the blend is uniform to achieve 0.0035 inch thickness. This blend is filtered using a cone type coarser filter paper to remove lumps. After completing these steps, the coating solution is ready to spray.

The coating is produced on the tubular body by a spray gun, preferably with an agitating pressure pot, although a spray gun without an agitating pressure pot may be used. The spraying process of the present invention preferably produces a nonuniform Teflon coating 360 degrees around the tubular body and extending continuously along the length of the tubular body 12. When applying the coating with the spray gun, rather than pulling the trigger all the way and holding it continuously, the trigger can be selectively depressed and released, or depressed with various degrees of pressure, as the gun passes from left to right over a portion of the tubular body. This process is repeated as the tubular body is rotated and a coating is applied 360 degrees around the tubular body. Coating on the tubular body by the spray gun can also be adjusted by controlling the flow rate of the spray exiting the gun. Moreover, the motion of the gun over the body allows control of the thickness and uniformity of the coating. These factors allow the coating 60 to be a thin, nonuniform coating covering substantially all of the tubular body, as shown in FIG. 4A.

Alternatively, the profile of the catheter can be reduced even further by spraying less than 360 degrees around the tubular body 12, as shown in FIG. 4B. The nonuniformity of the coating, thus, results from the tubular body 12 having portions that are coated with the polymer and other portions having no coating at all. The degree of nonuniformity depends on how the trigger of the spray gun is selectively activated and deactivated. Other methods to produce nonuniformity on the tubular body 12, such as masking portions of tubular body 12, may also be used. Moreover, the nonuniformity may result from the coating not being sprayed continuously over the circumference and/or length of the body.

After spraying, the coating should be flashed off to avoid any blistering. The coated tubular bodies are flashed off in an oven at 200° F. for 15 minutes. Then, the tubular body is cured. When a NiTi material is used for the tubular body, a curing temperature of about 540° F. is used in order to maintain the heat treated superelastic properties of NiTi. The curing step takes about one-half hour. After allowing the coated tubular bodies to cool, parts of the tubular body may be stripped to remove the coating from undesired areas. For instance, at the location of the proximal marker 62 shown in FIG. 1, no coating is desired. Suitable means for stripping include an abrasive and a razor blade, as well as other stripping means known to those skilled in the art.

Distal Marker

In another aspect of the present invention, a tubular marker 52, as shown in FIG. 2, is located within an adhesive taper 48 adjacent the balloon 22. Although the marker 52 is shown in the form of a tube, it will be appreciated by those skilled in the art that markers of other shapes may be used as well. To place the marker 52 within the taper 48, the marker is first slid over the coil 40 and core wire 38 and over the distal tip of the tubular body 12 past the inflation notch 36 so that it is out of the way for balloon bonding. Adhesive stops 32 and 34 and the balloon 22 are then mounted to the tubular body 12 using adhesives or other means known to those skilled in the art. One preferred method for mounting the adhesive stops and balloon to the tubular body is described in the above-referenced application BALLOON CATHETER AND METHOD OF MANUFACTURE (Attorney Docket PERCUS.010CP1), application Ser. No. 09/026,225, filed on the same day as the present application.

After balloon bonding, the marker 52 is slid towards the balloon 22 such that it is between about 0.5 and 3 mm from the proximal end of the balloon. More preferably, the marker 52 is located within about 1.0 mm from the proximal end 24 of the balloon 22. In the preferred embodiment shown in FIG. 2, the marker 52 is located about 0.75 mm from the balloon. The gap between the balloon 22 and the marker 52 is filled with an adhesive material taper 48. Preferably, a cyanoacrylate adhesive such as LOCTITE 4011 is used. However, as will be appreciated by those of skill in the art, other adhesives may be used. The taper 48 also extends from the proximal end 64 of the marker to point 66 on the tubular body 12, as well as from the proximal end 24 of balloon 22 to proximal end 64 of marker 52.

Because the marker is placed within the adhesive taper 48 of the balloon 22, the marker can be made larger and closer to the balloon, thereby increasing visibility without obstructing advancement of an aspiration catheter or the like when the tubular body 12 is used as a guidewire. Further details regarding an aspiration catheter are disclosed in assignee's co-pending application entitled ASPIRATION CATHETER, application Ser. No. 08/813,308, filed Mar. 6, 1997, the entirety of which is hereby incorporated by reference. The marker preferably has an outer diameter of at least about 0.02 inches. More preferably, the marker 52 has an inner diameter of about 0.017 inches and an outer diameter of about 0.024 inches. The proximal cyanoacrylate balloon taper 48 is preferably about 4 mm long, extending from point 24 on the balloon 22 to point 66 on the tubular body. The marker taper, extending from point 24 to distal point 68 on marker 52, is preferably about 0.75 mm long.

It will be appreciated that certain variations of the shaft of the present invention may suggest themselves to those skilled in the art. The foregoing detailed description is to be clearly understood as given by way of illustration, the spirit and scope of this invention being limited solely by the appended claims.

What is claimed is:

1. A catheter, comprising:

an elongate body having proximal and distal sections;

an expandable member mounted on the distal section of the tubular body, the expandable member having proximal and distal ends;

a marker mounted on the distal section of the elongate body adjacent the proximal end of the expandable member; and a taper formed from the proximal end of the expandable member in a proximal direction to the elongate body and covering the distal marker.

2. The catheter of claim 1, wherein the marker is a tube.

3. The catheter of claim 1, wherein the marker is radiopaque.

4. The catheter of claim 1, wherein the marker is located within about 3 mm of the proximal end of the expandable member.

5. The catheter of claim 1, wherein the taper is formed from a cyanoacrylate adhesive.

6. The catheter of claim 1, wherein the marker has an outer diameter of at least about 0.020 inches.

7. A catheter, comprising:

an elongate shaft;

a radiopaque marker for locating a desired point on the shaft; and an adhesive taper covering the marker.

8. A method of locating a desired point on a catheter when inserted inside a human body, comprising the steps of:

providing an elongate catheter shaft;

providing a radiopaque marker located at the desired point on the catheter shaft; and forming a taper covering the marker.

* * * * *